United States Patent [19]

Diessel et al.

[11] 4,410,449

[45] Oct. 18, 1983

[54] RECOVERY AND REUSE OF HEAVY-METAL OXIDATION CATALYST FROM THE WITTEN DMT PROCESS

[75] Inventors: Karl-Heinz Diessel, Nienburg; Rudolf Modic, Steyerberg; Friedrich Struss, Liebenau, all of Fed. Rep. of Germany

[73] Assignee: Dynamit Nobel Aktiengesellschaft, Troisdorf, Fed. Rep. of Germany

[21] Appl. No.: 407,619

[22] Filed: Aug. 12, 1982

Related U.S. Application Data

[63] Continuation of Ser. No. 215,340, Dec. 11, 1980, abandoned.

[30] Foreign Application Priority Data

Dec. 14, 1979 [DE] Fed. Rep. of Germany ....... 2950318
Oct. 1, 1980 [DE] Fed. Rep. of Germany ....... 2950318

[51] Int. Cl.$^3$ ...................... B01J 31/40; C07C 69/82; C07C 51/42; B01J 1/04
[52] U.S. Cl. .................................... 502/24; 210/688; 560/77; 560/78; 562/608; 502/28
[58] Field of Search ............... 252/411 R, 412, 413.1, 252/414, 415; 560/77-78; 562/414, 606-608; 210/688; 75/101 BE; 423/49, 50, 139, 150

[56] References Cited

U.S. PATENT DOCUMENTS

| | | | |
|---|---|---|---|
| 3,341,470 | 9/1967 | Hensley, Jr. ........................ | 562/414 |
| 3,780,096 | 12/1973 | Johnson et al. ..................... | 252/413 |
| 3,873,468 | 3/1975 | Kobinata et al. .................... | 252/413 |
| 3,956,175 | 5/1976 | Shigeyasu et al. .................. | 252/412 |
| 3,959,449 | 5/1976 | Shigeyasu et al. .................. | 423/488 |
| 4,096,340 | 6/1978 | Fujii et al. ............................ | 560/78 |
| 4,238,294 | 12/1980 | Takeuchi et al. .................... | 562/608 |
| 4,372,875 | 2/1983 | Bunger et al. ....................... | 252/413 |

FOREIGN PATENT DOCUMENTS

1239282 4/1967 Fed. Rep. of Germany .
2415393 3/1979 Fed. Rep. of Germany .
7411532 10/1974 France .

*Primary Examiner*—P. E. Konopka
*Attorney, Agent, or Firm*—Antonelli, Terry & Wands

[57] ABSTRACT

A process for the recovery and reuse of a heavy-metal oxidation catalyst solution from a high-boiling distillation residue having a cobalt content of 1-10 g/kg of residue is disclosed. The distillation residue is obtained in the production of dimethyl terephthalate by the oxidation of mixtures containing p-xylene and/or methyl p-toluate in the liquid phase with oxygen or an oxygen-containing gas under an elevated pressure and at an elevated temperature in the presence of dissolved heavy-metal oxidation catalyst, by subsequent esterification of the oxidation product with methanol and by a distillatory separation of the esterification product into a fraction rich in methyl p-toluate, a fraction rich in dimethyl terephthalate, and the high-boiling distillation residue. The process involves the steps of effecting extraction of the heavy-metal oxidation catalyst from the high-boiling distillation residue with aqueous low-molecular aliphatic monocarboxylic acids under heating; treating the aqueous, acidic extract, which contains the heavy-metal oxidation catalyst and has a cobalt content with a strongly acidic cation exchange resin in the alkali metal form at an elevated temperature until the exchange capacity has been reached, and washing the cation exchange resin at an elevated temperature with water and regenerating the cation exchange resin at room temperature with a solution containing Na$^+$ or K$^+$ acetate to displace the catalyst components and to obtain an aqueous acetic acid catalyst solution containing the catalyst components.

12 Claims, No Drawings

RECOVERY AND REUSE OF HEAVY-METAL OXIDATION CATALYST FROM THE WITTEN DMT PROCESS

This is a continuation of application Ser. No. 215,340, filed Dec. 11, 1980, now abandoned.

This invention relates to a process for the recovery and reuse of heavy-metal oxidation catalyst solution from the Witten process for producing dimethyl terephthalate (DMT), starting with high-boiling distillation residues having a cobalt content of 1–10 g/kg residue and in some cases a manganese content of 0.1–5 g/kg residue and/or a nickel content of 0.1–5 g/kg residue, obtained in the oxidation of reaction mixtures containing p-xylene (PX) and/or methyl p-toluate (PTE) in the liquid phase with oxygen-containing gases under elevated pressure, preferentially 4–10 bar and at elevated temperature, preferentially 140°–200° C. in the presence of dissolved heavy-metal oxidation catalyst, subsequent esterification of the oxidation product with methanol under elevated pressure, preferentially 20–30 bar, and at elevated temperature, preferentially 230°–280° C., and separation of the esterification product by distillation into a fraction rich in methyl p-toluate (PTE), a fraction rich in dimethyl terephthalate (DMT), and a high-boiling distillation residue, by extraction of the heavy-metal oxidation catalyst with dilute aqueous mineral acids or aqueous, low-molecular aliphatic monocarboxylic acids, under heating, optionally after combustion of the high-boiling distillation residues and dissolving the heavy metal oxidation catalyst in the combustion residue (ash) with mineral acids.

DMT is required as raw material for the production of polyester by reaction with ethylene glycol or tetramethylene glycol for fibers, filaments, films, or molded components. DMT is manufactured in numerous large-scale technical plants in accordance with the method which has become known as the "Witten process" or also the "Witten-Hercules" process.

Technically, the process is conducted by reacting the PX- und/or PTE-containing reaction mixture, in the absence of solvents and halogen compounds, in the presence of cobalt compounds and manganese compounds dissolved in the reaction mixture, to provide an oxidized product consisting predominantly of p-toluic acid (PTA), monomethyl terephthalate (MMT), and terephthalic acid (TPA), and esterifying the oxidized product at 230°–280° C. and 20–30 bar with methanol. The heavy-metal oxidation catalyst system is preferably employed in amounts, based on the quantity of oxidized product and converted to the metal content, of about 70–200 ppm cobalt and 2–100 ppm manganese. The esterification product is separated in a so-called raw ester distillation into a fraction rich in PTE, a fraction rich in DMT, as well as into a high-boiling distillation residue, by means of a distillation step. The fraction rich in PTE is introduced into the oxidation stage, the fraction rich in DMT is passed on to subsequent purification and working-up stages. The high-boiling residue contains, in addition to the organic components, the compounds of the heavy-metal oxidation catalyst system, e.g. cobalt and manganese.

It is technically feasible to feed high-boiling distillation residues of the oxidation of alkyl aromatics, from which no further useful products can be recovered any longer, be it by means of isolation or by means of conversion, to a combustion stage, optionally while utilizing the heat of combustion, and to separate the heavy-metal-containing ashes present in the flue gases of the combustion process by means of cyclones or electrostatic filters (see U.S. Pat. No. 3,341,470).

In DE-OS 22 60 498 (German Unexamined Laid-Open Application) a process is disclosed for the recovery of cobalt and manganese compounds out of residues of the production of aromatic carbonic acids, which residues are still containing iron and copper compounds, by, among other measures, extraction with dilute sulfuric acid and precipitating and separating, after stepwise raising the pH, iron hydroxide and the carbonates of cobalt and manganese. However, technical difficulties are encountered in the separation of such precipitates by filtration or centrifugation, as well as in the removal of the adhering, corresponding mineral acid by washing out of the filter cake.

The complete removal of the inorganic mineral acid residues is one of the prerequisites for reusing the heavy metals stemming from the high-boiling distillation residues as oxidation catalysts in the oxidation of alkyl aromatics in the liquid phase with atmospheric oxygen.

It is of extraordinary advantage for the DMT process to recover the oxidation catalyst, i.e. a mixture of cobalt compounds and manganese compounds and/or nickel compounds, from this high-boiling distillation residue by extraction, optionally after combustion of the residue, and reuse this catalyst for the oxidation of PX and/or PTE.

The invention furthermore presupposes that heavy metal components such as, for example, iron, chromium, vanadium, molybdenum, copper, and titanium are enriched in such ashes from the combustion of high-boiling distillation residues of the manufacturing process for alkyl aromatics by oxidation in the liquid phase in the presence of heavy-metal oxidation catalysts, which components stem from the materials of the manufacturing plant and from the fuels of the residue combustion, and which considerably reduce and/or inhibit the activity of the cobalt, manganese, or nickel catalyst and/or mixtures thereof when recycled into the oxidation reaction of the "Witten process".

It is an object of the present invention to recover, from the distillation residues of the raw ester distillation, the catalyst components, and to make available directly, without evaporation, the aqueous solutions suitable for use in the oxidation or for some other utilization of the valuable catalyst components either from the extract or from the dissolving of the combustion residue of said distillation residue with mineral acids.

The invention has the purpose of obtaining, from the acidic extracts or from the mineral acidic solutions a catalyst regenerate extensively free of interfering organic components and, furthermore, extensively free of metal compounds resulting from the materials of the manufacturing plant.

German Patent Application P 29 23 681 suggests a process for the recovery of oxidation catalyst from the catalyst-containing distillation residue obtained in DMT production, and for the reuse of the thusrecovered catalyst in the oxidation, with the objective of maintaining the selectivity of the oxidation at the same high level as in case of using fresh catalyst. It has been demonstrated therein that, in the extraction of the catalyst-containing distillation residue from the raw ester distillation, trimellitic acid (TMA) and the monomethyl ester of trimellitic acid (TMME) are dissolved together with the catalyst, and that TMA and TMME can considerably impair the course of the oxidation reaction when recycled into the oxidation stage with the catalyst. For this reason, in the aforementioned process, the quantitative ratio of TMA+TMME to the heavy-metal oxidation catalyst in the extract is set at a value of at most 1.8:1.

According to this invention, the content of TMA and TMME in the extract from the distillation residue can be higher by a multiple, for example, fivefold, than the content of cobalt-manganese catalyst, and thus can amount to almost three times the ratio of TMA+TMME to the heavy-metal oxidation catalyst admitted in the process of the German Patent Application P 29 23 681.

The content of TMA and TMME in the extract is dependent on the type of raw ester processing and thus on the chemical composition of the high-boiling distillation residue. With an increasing concentration of TMA and TMME in the extract, a raised consumption of heavy-metal oxidation catalyst is required to ensure a flawless progression of the oxidation reaction upon a recycling of the extracted catalyst.

Furthermore, the invention permits the recovery and reuse of cobalt compounds or cobalt and manganese compounds in conjunction with nickel compounds.

These objects have been attained by the invention. The object is attained, in a process of the above type, by the following steps:

(a) treating an aqueous, acidic extract, which contains the heavy-metal oxidation catalyst and has a cobalt content of 0.2–20 g/l also in some cases a manganese content of 0.05–10 g/l, and also in some cases a nickel content of 0.05–10 g/l, with a strongly acidic cation exchange resin in the alkali metal from, e.g. Na+ or K+ form, optionally at an elevated temperature until the exchange capacity has been reached; and (b) washing the cation exchange resin subsequently, optionally at an elevated temperature, and regenerating the cation exchange resin at room temperature with solutions containing Na+ or K+ acetate, thus displacing the catalyst components and obtaining an aqueous acetic acid solution containing the catalyst components.

The type of ion-exchanger used for the invention is based on polystyrene copolymerized with divinylbenzene and crosslinked. The active groups are bound sulfonic acid- (HSO₃-) groups. Suitable acidic cation exchange resins for use in the invention are Lewatit S 100, Amberlite IR 120, Dowex 50.

The temperatures used during the exchange treatment and the washing step preferably are between 10° C. and 90° C.

By means of the working up of the combustion products stemming from the high-boiling distillation residues, in accordance with this invention, it is possible in a simple way to obtain an aqueous, organic catalyst solution which is free of mineral acid residues and free of impurities, as TMA and TMME, inhibiting the activity of the oxidation metal catalyst components.

The thus-obtained aqueous catalyst solutions contain cobalt acetate and manganese acetate with a content of about 5–70 g/l of cobalt, 1–35 g/l of manganese, and in some cases nickel acetate with a content of about 1–35 g/l nickel. These aqueous solutions, containing the catalyst components as the acetates, are advantageously recycled directly into the oxidation of the mixtures containing p-xylene and/or methyl p-toluate.

Besides the cations of the alkali metal group, preferably sodium or potassium, the ion exchanger for adsorbing the catalyst metal components can also be used in the H+ ion form.

Preferably, the cation exchange resin, loaded with the catalyst metal ions, is regenerated with dilute aqueous sodium acetate solution because with the strongly acidic cation exchange resins used according to the invention the regeneration equilibrium

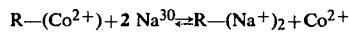

as compared to the regeneration equilibrium

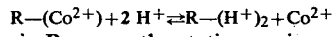

wherein R means the stationary ion exchange matrix, is oriented more into the direction of the right-hand side of the reaction equation.

By means of the treatment of the obtained extracts or solutions according to this invention with strongly acidic cation exchangers especially resins, an upward concentration of the catalyst metal content in the extract to values up to about 20 times the initial concentration is made possible in a surprisingly simple way, and in the case of extracting the distillation residue high contents of TMA and TMME are not interfering, by complex formation, in the exchange of the catalyst metal ions by the counter ion, e.g. the sodium ion on the cation exchanger resin.

According to the invention, there is no need for concentrating the extract by evaporation which, with increased TMA and TMME concentrations, would lead to losses of catalyst metal by precipitations and sedimentations. Rather, a quantitative separation of TMA and TMME, as well as other accompanying organic compounds, is attained in a simple manner. In view of the disturbances caused by considerable contents of TMA and TMME in the oxidation of mixtures containing PX and/or PTE, this result is of special value.

The process of this invention is conducted technically either by extraction of the distillation residue or by combustion of the distillation residue and subsequent processing with aqueous mineral acids and subjecting the solutions so obtained to the further processing as described herein.

In the case of extracting the distillation residue relative amounts by weight of the extracting agent are 0.3:1 to 5:1.

The percentage recovery of the cobalt, manganese and/or nickel present in the high-boiling distillation residue depends on the percentage recovery of the extraction step, optionally after combustion of the high-boiling distillation residues.

The percentage recovery of the cobalt, manganese and/or nickel in the combined steps a) and b) according to the invention is almost 100%, typically 98% and is ranging between about 95 and 99.9%.

The total percentage recovery of the cobalt, manganese and/or nickel in the overall process covered by the invention is about 85 to 99%. In a preferred embodiment the acidic, aqueous extracts are cooled from a temperature of about 95° C. to approximately room temperature, and the thus-precipitated organic components are separated. This is followed by reheating to about 70° C. to avoid subsequent precipitations. During the following loading of the strongly acidic cation exchanger in the Na+ form at about 70° C., any amounts of organic components, especially TMA, TMME, TPA, MMT and the like, still present in the extract, are not bound on the exchanger but rather in the aqueous phase and pass unhindered through the exchanger. In case this waste water, loaded primarily with alkali metal ions and organic compounds, cannot be passed on to biological processing but rather must be treated thermally, the alkali metal ions can be exchanged by treatment with a strongly acidic cation exchanger in the H$^+$ ion form, and removed by elution with a strong acid, preferably hydrochloric acid, in the form of the neutral salt, e.g. NaCl, in an aqueous solution. Upon reaching the exchange capacity with $Co^{2+}$ and $Mn^{2+}$, the loaded exchanger is treated with fully demineralized water, likewise heated to about 70° C., as the washing liquid. This treatment serves for removing of those organic components adsorbed on the exchange resin, which settle as a smeary film on the exchange resin matrix and would considerably reduce the exchange capacity if they were not removed with each cycle. The thus-produced washing water is suitably recycled into the extraction stage.

During the subsequent regeneration, conducted at room temperature about two bed volumes of an aqueous sodium acetate solution collected during the preceding regeneration cycle as the last runnings and having been combined with the forerunnings of the preceding regenerating cycle are introduced to the exchanger, loaded with $Co^{2+}$ and $Mn^{2+}$, the bed volume of which is initially filled with fully demineralized washing water. About 50% of the bed volume is withdrawn as a solution free of $Co^{2+}/Mn^{2+}$. Subsequently, about 15% of the bed volume is collected as forerunnings with a low $Co^{2+}/Mn^{2+}$ content. The next fraction withdrawn is about 135% of the bed volume as a $Co^{2+}/Mn^{2+}$ acetate solution (called concentrate hereinbelow). For a complete displacement of the catalyst metal components from the exchanger, about 80% of the bed volume of an approximately 15% aqueous sodium acetate solution containing about 10–15 g/l of free acetic acid is introduced onto the exchanger, and thereafter about 80% of the bed volume of fully demineralized water is fed onto the exchanger, in order to remove the sodium acetate solution which contains $Co^+$ and $Mn^+$ ions. The thus-obtained solutions, amounting in total to about 160% of the bed volume, are withdrawn, until a pronounced reduction in the $Co^{2+}/Mn^{2+}$ concentration, in an amount of about 5–10% of the bed volume, and combined with the concentrate, and the subsequent fractions in an amount of about 150–155% of the bed volume are discharged as the last runnings, combined with the previously obtained forerunnings, and reserved for use in the next regenerating cycle.

In case of processing the residues obtained from the combustion of the high-boiling distillation residues, which contain the heavy metal components including the metals of the oxidation catalyst, they are dissolved in mineral acids, e.g. hydrochloric acid or sulfuric acid, with the addition of oxidizing agents; for example, a hydrogen peroxide solution or nitric acid, to oxidize, inter alia, $Fe^{2+}$ ions. The impurities which have accumulated in the solution and stem from the materials of the plant and the fuels, such as for instance, iron, chromium, vanadium, molybdenum, copper and titanium, are then precipitated, by adjusting the solution to a pH of about 6 or thereabove, with, for example, aqueous sodium hydroxide solution, in the form of the hydroxides and the precipitates are filtered off together with the insoluble proportions of the combustion residue (ash). The thus-purified solution is adjusted to a pH of 5 or therebelow by adding at least one linear, low-molecular aliphatic monocarboxylic acid of 1–4 carbon atoms; for example, acetic acid. The $Na^{30}$ ions contained in the solution are removed by treatment with a strongly acidic cation exchange resin loaded with $Co^{2+}$, $Mn^{2+}$ and/or $Ni_{2+}$ ions. The resulting acetic-acid-containing heavy metal solution is then treated with a strongly acidic cation exchange resin in the $Na^+$ or $K^+$ form until the exchange capacity has been reached, and the cation exchange resin is subsequently washed, optionally at an elevated temperature, e.g. 50° to 90° C. and regenerated at room temperature with $Na^+$ or $K^+$ acetate-containing solutions, thus displacing the metal ions of the catalyst components and obtaining an aqueous, acetic acid solution which contains the metal ions of the catalyst components.

The combustion residue utilized in Examples 3 and 4 was obtained by burning a high-boiling distillation residue from the "Witten" DMT process at 800°–1200° C. and separation from the flue gases in an electrostatic filter. In this connection, 95% by weight of such a residue was combusted with the addition of 5% by weight of heavy fuel oil. The high-boiling distillation residue fed to the combustion contained about 0.1–1.0% by weight of heavy-metal components. The following examples serve for a further illustration of the invention.

EXAMPLE 1

100 kg of a distillation residue from the raw ester distillation was extracted with 60 l of reaction water of the DMT production with an acid content of about 3%, calculated as acetic acid, at about 95° C., to a residual $Co^{2+}$ content of 20 ppm; this distillation residue was obtained in an industrial plant for DMT production by the combined continuous oxidaton of PX- and PTE-containing mixtures in the liquid phase with atmospheric oxygen under 8 bar pressure and at temperatures of 150°–170° C. with the use of a solution of cobalt acetate and manganese acetate in aqueous acetic acid, a stationary concentration of about 90 ppm cobalt and 10 ppm manganese being set in the oxidation product; subsequent continuous esterification of the oxidation product at temperatures of about 250° C. and under 25 bar pressure with methanol; and continuous separation of the esterification product by vacuum distillation, wherein, in a first distillation column, a fraction rich in PTE is withdrawn overhead and recycled into the oxidation, and the sump product of this column is separated in a second, subsequent column in to a fraction rich in DMT, withdrawn overhead, and into a high-boiling distillation, residue having a cobalt content of 2.3 g/kg and a manganese content of 0.2 g/kg of residue.

After decanting, 56 l of a $Co^{2+}/Mn^{2+}$-containing extract was obtained having a $Co_{2+}$ content of 3.8 g/l and a $MN^{2+}$ content of 0.3 g/l. The hot extract was cooled to 20° C. and thus-precipitated organic compounds were separated by filtration.

The filtered solution was heated to 70° C. to prevent subsequent precipitation and passed from below through a tube charged with a strongly acidic cation exchanger loaded with $Na^+$ ions commercially available under the name of "Lewatit S 100". The resin volume was 1.1 l. The loading was continued until the incipient exhaustion of the ion exchange capacity.

From the resulting 56 l of Co-Mn extract, 19 l, corresponding to a total content of 78.4 g $Co^{2+}$ +$Mn^{2+}$ or 2.66 eq. $Co^{2+}$, was conducted at 70° C. over the cation exchanger. Subsequently, the cation exchanger was washed with fully demineralized water introduced from the top at 70° C. Thereupon, the cation exchanger was eluted from the top with 2.2 l of a 10% aqueous acetic-acid sodium acetate solution, corresponding to 1.3 eq. $Na^+/l$, and then a subsequent washing step was conducted with 1 l of fully demineralized water at room temperature, thus obtaining 0.4 l of forerunnings, 2.0 l of aqueous concentrate, and 0.8 l of last runnings.

The forerunnings contained 4.8 g/l $Co^{2+}$, 0.4 g/l $Mn^{2+}$ and 0.8 g/l $CH_3COOH$.

The last runnings contained 11.2 g/l $Co^{2+}$, 0.9 g/l $MN^{2+}$, 9.5 g/l $Na^+$ and 6.3 g/l $CH_3COOH$.

The aqueous concentrate contained the following components:

| | | |
|---|---|---|
| $Co^{2+}$ | = | 30.1 g/l |
| $Mn^{2+}$ | = | 2.6 g/l |
| $Na^+$ | = | 1.0 g/l |
| $CH_3COOH$ | = | 12.0 g/l |
| Organic Impurities | | cannot be detected (polarographically) |

The thus-obtained $Co^{++}$, $Mn^{++}$ containing and the $Na^+$ containing forerunnings and last runnings, respectively, were combined and utilizedagain as the eluting solution to avoid $Co^{++}$ and $Mn^{++}$ losses.

EXAMPLE 2

In a continuously operating extraction plant, 300 kg/h of the highboiling distillation residue of the raw ester distillation obtained as in Example 1 was extracted under agitation at about 95° C. with 150 kg/h of acidic reaction water from the DMT production, the origin and acid content of which were in correspondence with Example 1.

The aqueous solution obtained after separation of the organic phase contained 4.6 g/l of $Co^{2+}$ and 0.4 g/l of $Mn^{2+}$. This solution was cooled to about 20° C. and separated by filtration from the precipitated organic products, which were recycled into the process, and was then collected in a container. After heating to about 70° C. to avoid subsequent precipitation of organic compounds, 650 l/h of this solution was conducted at a temperature of 70° C. over a column charged with 180 l of a resin loaded with $Na^+$ ions under the commercial name of "Lewatit S 100". The loading of the exchanger was completed after about 3 hours.

Thereafter, a flushing step was conducted with 400 l of hot, demineralized water in order to remove organic compounds. Subsequently, the catalyst ions were eluted at approximately room temperature with a solution containing sodium acetate and with a content of 10–15 g/l of free acetic acid consisting, in part, of the forerunnings and last runnings of the preceding elution as well as a 15% sodium acetate solution. In total, 515 l of solution was used for eluting purposes. After elution, the exchanger was washed with 170 l of fully demineralized water.

Four fractions were collected: 90 l $Co^{++}$- and $Mn^{++}$-free solution, 35 l of forerunnings, 240 l of concentrate, and 320 l of last runnings.

The forerunnings contained 5.8 g/l $Co^{2+}$, 0.4 g/l $Mn^{2+}$ and 1.0 g/l $CH_3COOH$.

The last runnings contained 16.6 g/l $Co^{2+}$, 1.3 g/l $Mn^{2+}$, 19.4 g/l $Na^+$ and 10.8 g/l $CH_3COOH$.

The concentrate contained
37.0 g/l $Co^{++}$ and
3.1 g/l $Mn^{++}$.

No organic components except for acetic acid could be detected by polarography. The forerunnings and last runnings were combined and reused for the subsequent cycle. The concentrate was recycled directly into the oxidation described in Example 1. The activity of this concentrate was identical to that of a fresh catalyst solution having the same cobalt and manganese acetate concentration.

EXAMPLE 3

By combustion of 25 kg of a distillation residue, obtained analogously as in Example 1, having a cobalt content of 0.23 weight %, a manganese content of 0.025 weight % and traces of iron, nickel, chromium, molybdenum, copper and titanium, with heavy fuel oil, 113.3 g of a combustion residue were obtained.

50.5 g of said combustion residue from the DMT process was processed under agitation with 300 ml of dilute HCl solution (=12% HCl) and 2 ml of 30% $H_2O_2$ solution for two hours at 95° C.

The combustion residue employed contained:

| | |
|---|---|
| 50.7% | by weight cobalt |
| 5.4% | by weight manganese |
| 0.37% | by weight iron |
| 0.13% | by weight nickel |
| 100 ppm | chromium |
| 1,000 ppm | molybdenum |
| 100 ppm | vanadium |
| 100 ppm | copper |
| 100 ppm | titanium. |

The solution was then diluted with 1 liter of fully demineralized water and combined with about 40% strength sodium hydroxide solution to pH 7. The amount of sodium hydroxide solution consumed was 9 ml. The solution was then heated for one hour to 95° C. and filtered through a folded filter.

The filtrate, after dilution with fully demineralized water, was adjusted to a volume of 8 liters and to pH 4 with 5 ml of concentrated acetic acid.

The solution contained:

| | |
|---|---|
| 2.9 g | cobalt/l |
| 0.2 g | manganese/l |
| 6 ppm | nickel |
| <5 ppm | iron |
| <5 ppm | chromium, molybdenum, vanadium, copper, titanium |

The thus-obtained solution was conducted, to extensively remove the $Na^+$ ions, through a column with 250 ml of a strongly acidic cation exchange resin loaded with $Co^{2+}$ and $Mn^{2+}$ ions.

A column with 250 ml of strongly acidic cation exchange resin "Lewatit S 100" in the $Na^+$ form was charged with the solution.

The waste water obtained at the discharge end contained:
30 ppm cobalt
2 ppm manganese.

The exchanger was loaded with 3.5 l of the above solution until incipient exhaustion (limit value - 300 ppm cobalt in the effluent).

The exchanger was then washed with 250 ml of fully demineralized water.

The cobalt and manganese ions were eluted with the following solutions:

400 ml of combined forerunnings and last runnings fractions from the preceding experiment
200 ml of an 18% strength sodium acetate solution with 15 g of free acetic acid per liter
200 ml of fully demineralized water.

The forerunnings contained 4.2 g/l $Co^{2+}$, 0.3 g/l $Mn^{2+}$ and 0.6 g/l $CH_3COOH$ (free acid).

The last runnings contained 20.5 g/l $Co^{2+}$, 1.4 g/l $Mn^{2+}$, 18.7 g/l $Na^+$ and 8.7 g/l $CH_3COOH$ (free acid).

The elution yielded:
60 ml of a forerunnings fraction
400 ml of a main fraction depleted of $Na^+$
340 ml of a last runnings fraction rich in $Na^+$.

The forerunnings and last runnings were combined and utilized for elution purposes during the subsequent experiment.

The main fraction contained:

| | |
|---|---|
| 30.9 | g cobalt/liter |
| 2.1 | g manganese/liter |
| 75 | ppm nickel |
| <5 | ppm chromium, molybdenum, vanadium, copper, titanium |
| 175 | ppm sodium. |

The thus-obtained main fraction can be utilized as the catalyst solution in the DMT process.

EXAMPLE 4

By combustion of 25 kg of a distillation residue, obtained analogously as in Example 1, having a cobalt content of 0.20 weight %, a manganese content of 0.020 weight %, a nickel content of 0.10 weight % and traces of iron, chromium, molybdenum, copper and titanium, with heavy fuel oil, 120.2 g of a combustion residue were obtained.

50.1 g of said combustion residue was made into a solution with 350 ml of 12% hydrochloric acid and 2 ml of 30% $H_2O_2$ solution for 2 hours at 95° C.

The combustion residue utilized contained:

| | |
|---|---|
| 40.6% | by weight Co |
| 4.3% | by weight Mn |
| 19.8% | by weight Ni |
| 2,970 | ppm Fe |
| <100 | ppm Cr |
| 800 | ppm Mo |
| <100 | ppm V |
| 80 | ppm Cu |
| <100 | ppm Ti |
| 1,280 | ppm Na. |

The resulting solution was adjusted to pH 6.2 with 7 ml of an approximately 40% strength sodium hydroxide solution. After one hour, the solution, heated to 95° C., was filtered through a folded filter. The filtrate was diluted to 10 l with fully demineralized water and adjusted to pH 3.9 with 10 ml of concentrated acetic acid.

The solution contained:

| | |
|---|---|
| 1.84 | grams Co/liter |
| 0.16 | grams Mn/liter |
| 0.87 | grams Ni/liter |
| <5 | ppm Fe |
| <5 | ppm Cr |
| <5 | ppm Mo |
| <5 | ppm V |
| <5 | ppm Cu |
| <5 | ppm Ti. |

The thus-obtained solution was treated, to extensively remove the $Na^+$ ions, with 250 ml of a strongly acidic cation exchange resin loaded with $Co^{2+}$, $Mn^{2+}$, and $Ni^{2+}$ ions, A column with 250 ml of a strongly acidic cation exchange resin "Lewatit S 100" in the $Na^+$ form was charged with the resulting solution.

The waste water obtained at the discharge end contained:
25 ppm Co
2 ppm Mn
10 ppm Ni, To load the exchanger until incipient exhaustion, 4.7 liters of the solution was consumed. The exchanger was then washed with 250 ml of fully demineralized water.

For eluting the $Co^{2+}$, $Mn^{2+}$, and $Ni^{2+}$ ions, the following solutions were employed:
390 ml of combined forerunnings and last runnings fraction of the preceding experiment
200 ml of an 18% sodium acetate solution containing 15 g of free acetic acid per liter
210 ml of fully demineralized water, The forerunnings contained 3.6 g/l $Co^{2+}$, 0.3 g/l $Mn^{2+}$, 1.8 g/l $Ni^{2+}$ and 0.5 g/l $CH_3COOH$ (free acid). The last runnings contained 13.4 g/l $Co^{2+}$, 1.3 g/l $Mn^{2+}$, 7.2 g/l $Ni^{2+}$ 8.9 g/l $CH_3COOH$ (free acid) and 15.8 g/l $Na^+$.

The following solutions were obtained during elution:
80 ml of a forerunnings fraction
400 ml of a main fraction depleted of $Na^+$ ions
320 ml of a last runnings fraction rich in $Na^+$ The main fraction contained:

| | |
|---|---|
| 21.5 | grams Co/liter |
| 1.9 | grams Mn/liter |
| 10.2 | grams Ni/liter |
| <5 | ppm Fe |
| <5 | ppm Cr |
| <5 | ppm Mo |
| <5 | ppm V |
| <5 | ppm Cu |
| <5 | ppm Ti |
| 240 | ppm Na. |

What is claimed is:

1. A process for the recovery and reuse of a heavy-metal oxidation catalyst solution from a high-boiling distillation residue having a cobalt content of 1–10 g/kg of residue, which is obtained in the production of dimethyl terephthalate by the oxidation of mixtures containing p-xylene and/or methyl p-toluate in the liquid phase with oxygen or an oxygen-containing gas under a pressure of 4–10 bar and at a temperature of 140°–200° C. in the presence of dissolved heavy-metal oxidation catalyst, by subsequent esterification of the oxidation product with methanol under a pressure of 20–30 bar and at a temperature of 230°–280° C., and by a distillatory separation of the esterification product into a fraction rich in methyl p-toluate, a fraction rich in dimethyl terephthalate, and the high-boiling distillation residue, which comprises effecting extraction of the heavy-metal oxidation catalyst from the high-boiling distillation residue with aqueous low-molecular aliphatic monocarboxylic acids of 1–4 carbon atoms, under heating, treating the aqueous, acidic extract, which contains the heavy-metal oxidation catalyst and has a cobalt content of 0.2–20 g/l with a strongly acidic cation exchange resin in the alkali metal form at an elevated temperature until the exchange capacity has been reached, and washing the cation exchange resin at an elevated temperature with water and regenerating the cation exchange resin at room temperature with a solution containing $Na^{30}$ or $K^+$ acetate, thus displacing the catalyst components and obtaining an aqueous acetic acid catalyst solution containing the catalyst components.

2. A process according to claim 1, wherein the high-boiling distillation residue has a manganese content of 0.1–5 g/kg of residue and said aqueous extract further contains a mananese content of 0.05–10 g/l.

3. A process according to claim 1, wherein the high-boiling distillation residue has a manganese content of 0.1–5 g/kg of residue and/or a nickel content of 0.1–5 g/kg of residue and said aqueous extract further contains a magnesium content of 0.05–10 g/l and a nickel content of 0.05–10 g/l.

4. A process according to claim 1, wherein the alkali metal form of the strongly acidic cation exchange resin is either the $Na^{30}$ or $K^+$ form.

5. A process for the recovery and reuse of a heavy-metal oxidation catalyst solution from a high-boiling distillation residue having a cobalt content of 1–10 g/kg of residue, which is obtained in the production of dimethyl terephthalate by the oxidation of mixtures containing p-xylene and/or methyl p-toluate in the liquid phase with oxygen or an oxygen-containing gas under a pressure of 4–10 bar and at a temperature of 140°–200° C. in the presence of dissolved heavy-metal oxidation catalyst, by subsequent esterification of the oxidation product with methanol under a pressure of 20–30 bar and at a temperature of 230°–280° C., and by a distillatory separation of the esterification product into a fraction rich in methyl p-toluate, a fraction rich in dimethyl terephthalate, and the high-boiling distillation residue; which comprises (a) effecting combustion of the high-boiling residue to form ashes;

(b) obtaining an acidic extract by extracting the ashes resulting after combustion of the high-boiling distillation residue with aqueous mineral acids with the addition of oxidizing agents under heating, by subsequently diluting with water, by increasing the pH of the diluted extract with the addition of an alkali to precipitate iron and chromium as the hydroxides, by filtering to effect the combined removal of the hydroxides as well as insoluble ash components, by effecting dilution with water, then by effecting acidification of the filtrate with acetic acid, and by effecting removal of the $Na^+$ ions contained in the filtrate with the aid of a strongly acidic cation exchange resin loaded with $Co^{2+}$, $Mn^{2+}$ and/or $Ni^{2+}$ ions;

(c) treating the aqueous, acidic extract, which contains the heavy-metal oxidation catalyst and has a cobalt content of 0.2–20 g/l with a strongly acidic cation exchange resin in the alkali metal form at an elevated temperature until the exchange capacity has been reached; and (d) washing the cation exchange resin at an elevated temperature with water and regenerating the cation exchange resin at room temperature with a solution containing $Na^+$ or $K^+$ acetate, thus displacing the catalyst components and obtaining an aqueous acetic acid catalyst solution containing the catalyst components.

6. A process according to claim 5, wherein the cobalt or cobalt and manganese compounds, together with nickel compounds, are obtained from extracts of ashes from the combustion of the high-boiling cobalt-, cobalt- and manganese-containing, cobalt- and nickel-containing, or cobalt-, manganese- and nickel-containing distillation residues with a content of 0.2–20 g/l of cobalt, 0.05–10 g/l of manganese and 0.05–10 g/l of nickel, respectively.

7. A process according to claim 5, wherein the catalyst components are obtained from the ashes of the combustion of the high-boiling distillation residues by treatment with aqueous hydrochloric acid with the addition of aqueous $H_2O_2$ at about 95° C., for a duration of 0.1–4 hours, by subsequent increasing the pH value to a value of at least 6 with the addition of aqueous alkalis, by heating to about 95° C. for 0.1–2 hours, by effecting the combined removal of the thus-formed hydroxides of iron, chromium, as well as the insoluble ash components with filtration, and by effecting acidification of the filtrate with acetic acid to pH 5 or lower.

8. A process according to claim 5, wherein the catalyst solution obtained according to step (b) contains cobalt acetate and manganese acetate with a content of 10–70 g/l of cobalt, as well as less than respectively 5 mg of iron/l, 5 mg of chromium/l, 5 mg of molybdenum/l, 5 mg of vanadium/l, 5 mg of copper/l, and 5 mg of titanium/l.

9. A process according to one of claims 6, 7 and 5, wherein said high-boiling distillation residue has a manganese content of 0.1–5 g/kg of residue and the aqueous acidic extract has additionally a manganese content of 0.05–10 g/l.

10. A process according to one of claims 6, 7 and 5, wherein said high-boiling distillation residue further contains a manganese content of 0.1–5 g/kg of residue and a nickel content of 0.1–5 g/kg of residue and said aqueous acidic extract further contains a manganese content of 0.05–10 g/l and a nickel content of 0.05–10 g/l.

11. A process according to claim 9, wherein the catalyst solution obtained according to step (b) contains cobalt acetate and manganese acetate with a content of 10–70 g/l of cobalt and with a content of 1–35 g/l of manganese as well as less than, respectively, 5 mg of iron/l, 5 mg of chromium/l, 5 mg of molybdenum/l, 5 mg of vanadium/l, 5 mg of copper/l and 5 mg of titanium/l.

12. A process according to claim 10, wherein the catalyst solution obtained according to step (b) contains cobalt acetate, manganese acetate, and nickel acetate with a content of 10–70 g/l of cobalt, 1–35 g/l of manganese, and 1–35 g/l of nickel, as well as less than respectively 5 mg of iron/l, 5 mg of chromium/l, 5 mg of molybdenum/l, 5 mg of vanadium/l, 5 mg of copper/l, and 5 mg of titanium/l.

* * * * *